(12) United States Patent
Kientz

(10) Patent No.: US 10,287,540 B2
(45) Date of Patent: May 14, 2019

(54) CONSTRUCTION METHOD OF A FERMENTER FOR A BIOGAS PLANT

(71) Applicant: HITACHI ZOSEN INOVA AG, Zürich (CH)

(72) Inventor: Hans-Peter Kientz, Singen (DE)

(73) Assignee: HITACHI ZOSEN INOVA AG, Zürich (CH)

( * ) Notice: Subject to any disclaimer, the term of this patent is extended or adjusted under 35 U.S.C. 154(b) by 595 days.

(21) Appl. No.: 14/897,336

(22) PCT Filed: Jun. 6, 2014

(86) PCT No.: PCT/EP2014/061841
§ 371 (c)(1),
(2) Date: Dec. 10, 2015

(87) PCT Pub. No.: WO2014/198667
PCT Pub. Date: Dec. 18, 2014

(65) Prior Publication Data
US 2016/0130544 A1    May 12, 2016

(30) Foreign Application Priority Data

Jun. 10, 2013  (CH) .................................. 1092/2013

(51) Int. Cl.
| | | |
|---|---|---|
| *C12M 1/12* | (2006.01) | |
| *C12M 1/107* | (2006.01) | |
| *C12M 3/04* | (2006.01) | |

(52) U.S. Cl.
CPC ............ *C12M 23/06* (2013.01); *C12M 21/04* (2013.01); *C12M 27/10* (2013.01); *Y02E 50/343* (2013.01)

(58) Field of Classification Search
CPC ...... C12M 23/06; C12M 27/10; C12M 21/04; Y02E 50/343
See application file for complete search history.

(56) References Cited

U.S. PATENT DOCUMENTS

| | | | | |
|---|---|---|---|---|
| 2,287,198 A | * | 6/1942 | Sandberg | ............... B21D 51/00 220/565 |
| 5,169,782 A | * | 12/1992 | Murphy | ................ B01F 9/0007 435/290.3 |
| 6,942,139 B2 | * | 9/2005 | Lipnevicius | ......... B23K 9/0216 228/102 |

FOREIGN PATENT DOCUMENTS

| | | |
|---|---|---|
| EP | 0 794 247 A1 | 9/1997 |
| GB | 2144767 * | 3/1985 |

(Continued)

OTHER PUBLICATIONS

Sep. 30, 2014 International Search Report issued in International Patent Application No. PCT/EP2014/061841.

(Continued)

*Primary Examiner* — John C Hong
(74) *Attorney, Agent, or Firm* — Oliff PLC

(57) ABSTRACT

A construction method of a fermenter, which has a fermenter cage and a fermenter shell made of metal, for use in a biogas plant, wherein the fermenter shell surrounds the fermenter cage making the fermenter shell gas-tight. The fermenter cage is formed by a plurality of cage rings, wherein each cage ring is supported on at least one cage-retaining device having at least one rolling device in such a way that the entire fermenter cage is rotatably supported about a longitudinal axis, wherein the fermenter cage is lined with a plurality of rows of shell plates by way of rotation about the longitudinal axis and the shell plates are permanently fastened to the inner surfaces of the plurality of cage rings and thus the fermenter shell is formed.

19 Claims, 6 Drawing Sheets

(56) References Cited

FOREIGN PATENT DOCUMENTS

WO      2009/134857  A1    11/2009
WO      2012/169983  A2    12/2012

OTHER PUBLICATIONS

Dec. 15, 2015 International Preliminary Report on Patentability issued in International Patent Application No. PCT/EP2014/061841.

* cited by examiner

CONSTRUCTION METHOD OF A FERMENTER FOR A BIOGAS PLANT

TECHNICAL FIELD

The present invention describes a construction method of a fermenter having a fermenter cage and a fermenter shell made of metal, for use in a biogas plant, as well as a fermenter.

PRIOR ART

A fermenter from the applicant for biogas plants having a fermenter interior of about eighteen hundred cubic meters and made from a steel structure is already known. This fermenter comprises a fermenter cage with several metal cage rings. With the known manufacturing method the cage rings are in a first step set up vertically on cage-retaining devices and fixed with pendulum supports. The cage rings form a fermenter cage, in the interior of which are arranged and fixed several shell plates. The shell plates are each welded to the adjoining shell plates so that a cylindrical, gas-tightly closed fermenter shell is formed around the fermenter cage.

Constructing a fermenter of this kind requires about four months of construction time, whereby a high amount of preliminary production work has to be undertaken. Setting up the cage rings requires a large portal crane, which can combine individual ring segments on site into retaining rings. A portal crane of this kind is not available at every construction site so that it has to be supplied separately. Furthermore, setting up and dismantling a portal crane of this kind is also laborious and time-comsuming.

Once the cage rings are fixed on the cage-retaining devices, one can then start with placing and fixing the pre-curved shell plates. The shell plates used up until now were pre-curved in factory production to match the curvature of the cage rings and then transported to the construction site. Apart from the laborious bending of the shell plates there is also a problem with conveying the factory-made components. Transporting the shell plates, which are about 8 meters long and 3 meters wide, requires an appropriate vehicle, as well as supporting devices on the vehicle. This can involve high costs depending on how far the journey route is to the construction site.

The shell plates are introduced into the fermenter cage interior adjacent to one another and then welded firmly there. The shell plates are then fixed to the interior faces of the cage rings and on longitudinal welding seams running between adjacent shell plates. Welding must be carried out carefully so that a gas-tight fermenter is later obtained. The shell plates are for this purpose welded to surround the entire fermenter cage and line the entire fermenter cage in a laborious manner, in part overhead. Welding that can be satisfactorily reproduced is difficult, very time-consuming and can usually only be carried out by specially trained personnel. Gas-tight welding is however essential.

After lining the fermenter cage with the shell plates in a gas-tight manner, wall structures could be fastened on the inlet side and outlet side to the fermenter cage. In order to place a required agitator unit in the fermenter cage, however, the end wall structures, as well as the shell plates in the region of the fermenter cage cover, had to be removed once again in order to let the agitator unit pass through the cover region into the interior of the fermenter cage. This process has severely complicated and lengthened the construction time of known fermenters that are provided with fermenter cages and fermenter shells of this kind.

From the document WO 2009/134857 A1, a composter is known, which is formed from several partial cylinders. These partial cylinders consist in turn of pre-curved panels, which are brought together in a first step. Only after combining the partial cylinders is the resulting composter provided with a rolling device. The rolling device is mounted such that the entire composter is rotated about a longitudinal axis during operation. During the construction of the composter from WO 2009/134857 A1, the panels are laboriously welded to one another by means of an additional welding table.

The composter known from WO 2009/134857 A1 thus has the drawback that the construction is very complicated. Pre-curved panels are used, which have to be supplied to the construction site. A further drawback is that additional special equipment, such as the welding table, is necessary during construction.

Presentation of the Invention

The object of the present invention is to provide a construction method of fermenters in steel construction, which can be carried out with a considerably reduced construction time, with reduced use of special equipment, and with few factory construction steps, so that fermenters can be erected in considerably shorter construction times than is known from the prior art.

The aim is to significantly reduce the transport costs and the transport effort and to provide possibilities for local sourcing of semi-finished products.

This problem is solved through the implementation of the method according to the present invention having the features of patent claim 1. By means of the method according to the present invention, it is possible to achieve a significantly more cost-effective construction of fermenters of this kind.

When carrying out the present construction method, standard materials, such as by way of example simple unbent sheet steel plates as shell plates, are extensively used.

BRIEF DESCRIPTION OF THE DRAWINGS

A preferred exemplary embodiment of the subject of the present invention will now be described in connection with the accompanying drawings, in which

FIG. 4a shows a perspective view of a first cage ring, which is mounted vertically upright on an associated cage-retaining device; while

FIG. 7 shows a perspective view of a fermenter cage with a wall structure attached on the output side; while

DESCRIPTION

Figure 1:
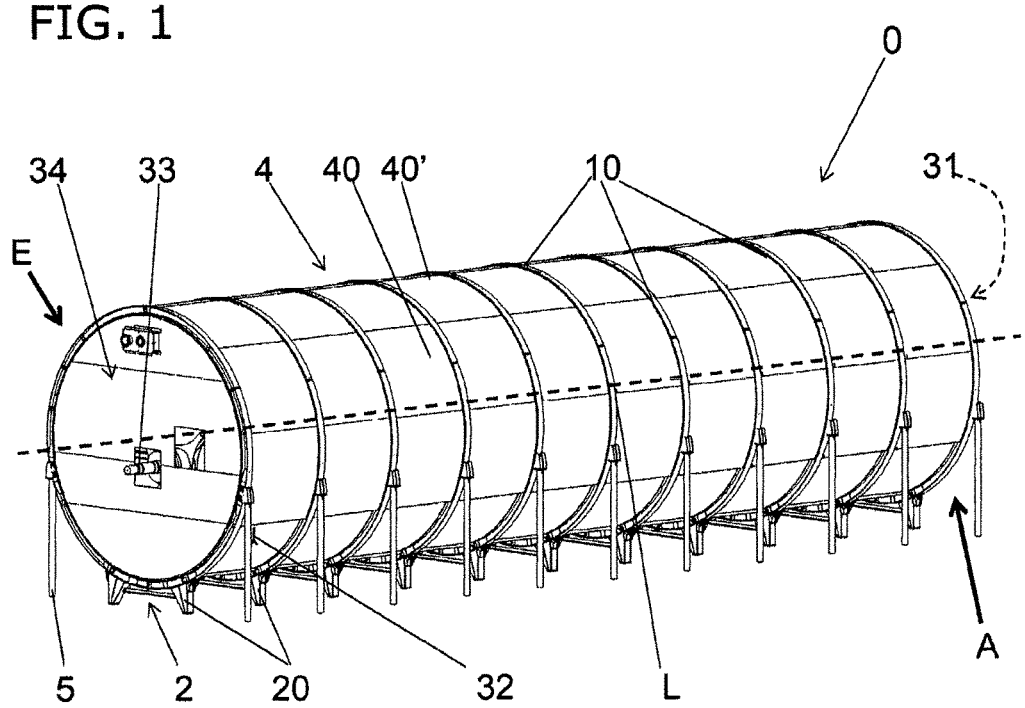
FIG. 1 shows a perspective view of a finished operationally-ready fermenter in the operating position supported on stabilizing supports.
Figure 7:
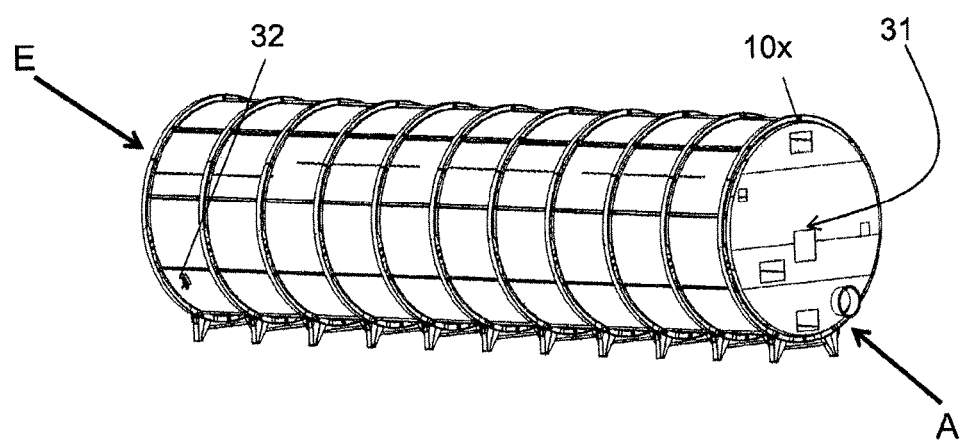

FIG. 1 shows a finished gas-tight fermenter 0 oriented in the position of use, which can be part of a biogas plant. The fermenter 0 extends in a roughly horizontal direction from an input side E along its longitudinal axis L to an output side A. The input side E is closed off by a wall structure on the input side, whilst the output side A is closed off by a wall structure 31 on the output side, as shown more clearly in FIG. 7. A plurality of x cage rings 10 forms a fermenter cage as the basic framework for the fermenter 0. The fermenter cage is described in detail below, but in FIG. 1, it is covered by an insulation shell 4 that comprises several insulation elements 40. An agitator unit 33 as well as a heating system 32 are housed in this fermenter cage. The cage rings 10 are each mounted on a cage-retaining device 2, wherein here each two holders 20 hold one cage ring 10. In the operationally-ready state of the fermenter 0, additional stabilizing supports 5 are fixed to the cage rings 10 in the lower half and on the sides, so that a secured stable position of the fermenter 0 can be reached.

Figure 2:
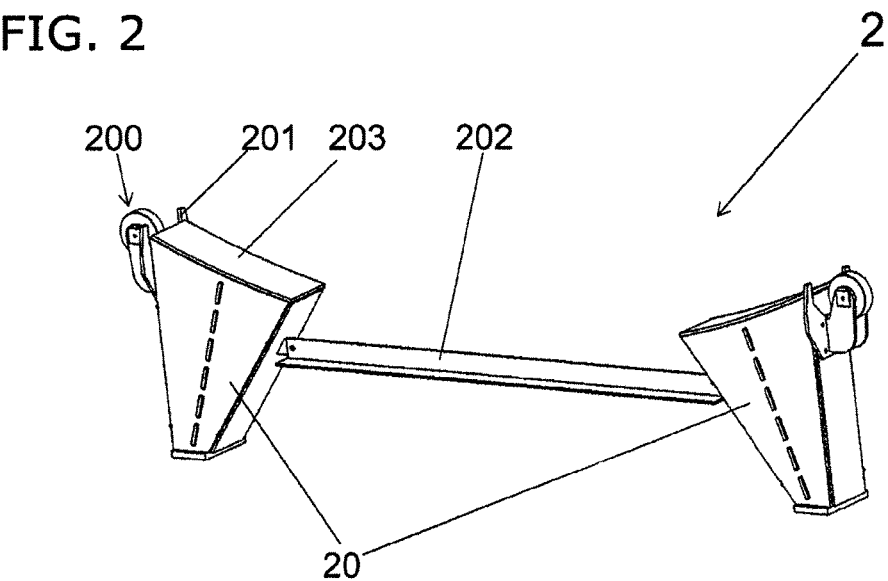
FIG. 2 shows a perspective view of a cage-retaining device, comprising two holders, which each have a rolling device.
Figure 3A:
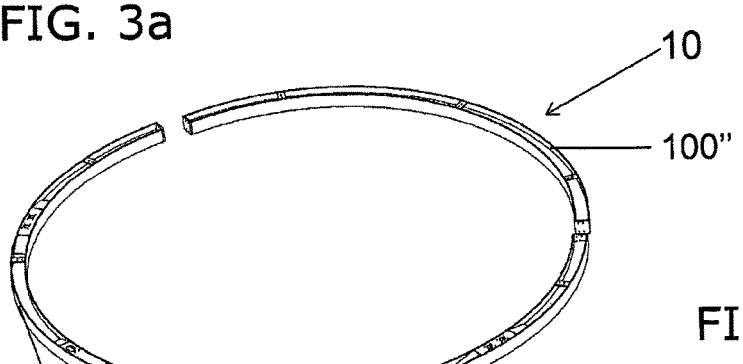
FIG. 3 a) shows a perspective view of three ring segments that form a closed cage ring according to FIG. 3b)
Figure 3B:
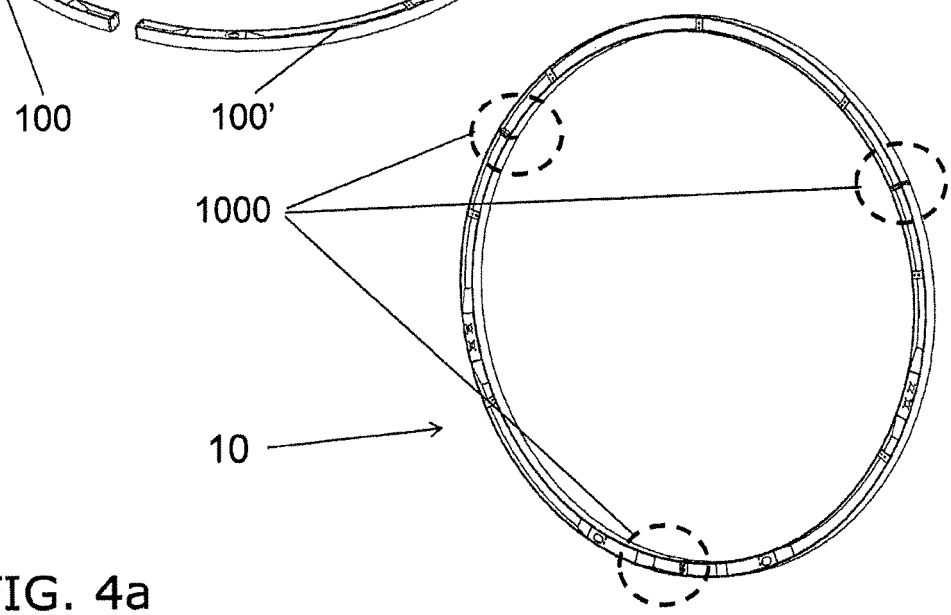

In order to carry out the construction method according to the present invention, the cage rings 10 are mounted on cage-retaining devices 2, such as shown by way of example in FIG. 2. Each two holders 20 are connected by a retaining brace 202. Each of the holders 20 has a rolling device 200 and a support surface 203. The support surface 203 is here matched to the curvature of the cage rings 10. To avoid that the cage rings 10 slide down from the support surface 203 or from the rolling device 200, a guideway 201 is provided, which is here shaped in the manner of a fork. The rolling device 200 and the guideway 201 are detachably fastened to each holder 20. All the components are preferably made from steel.

A cage-retaining device 2 can optionally be provided with only one holder 20 that has to be correspondingly formed so that the cage ring 10 stands stable.

In order to achieve a simple transport of the components for the fermenter construction, the already introduced cage rings 10 are designed in several parts. Here, three ring segments 100, 100', 100" are provided, which are pre-curved correspondingly in order to form a closed cage ring 10. The ring segments 100, 100', 100" used are double T-supports and consist of an IPB240 standard support according to DIN 1025-2 and were bent cold. A flange plate is welded to the ends of each ring segment 100, 100', 100", thus in the region of the connecting spots 1000. After being brought together, adjacent ring segments 100, 100', 100" can be connected semi-detachably to one another by several retaining ring bolts. Other connecting methods are likewise possible, but preferably the connection is by means of retaining ring bolts, since a simple and rapid connection is necessary without checking a welding seam or the torque of, for example, screws.

Figure 4A:
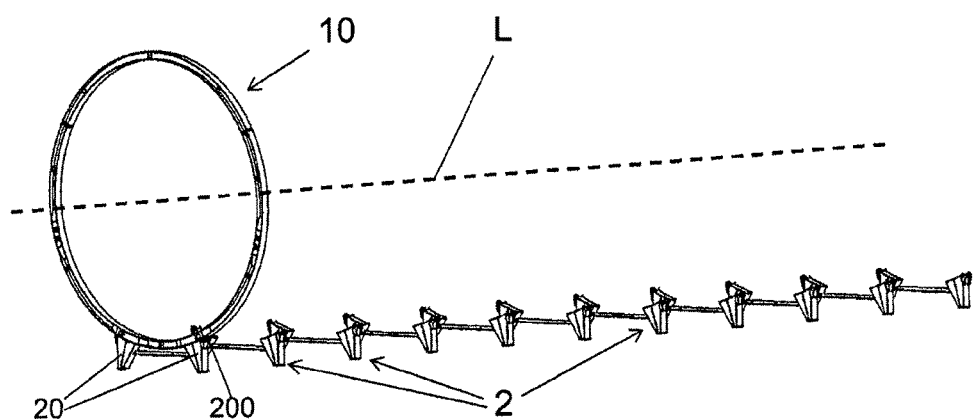
Figure 4B:
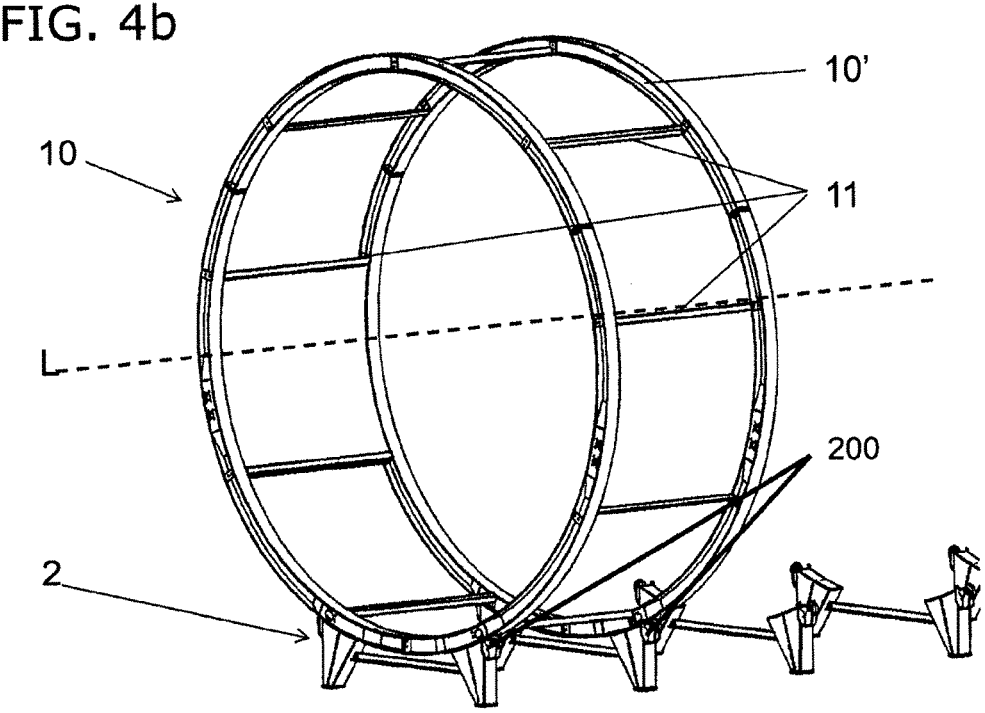
FIG. 4b shows the connection of two adjacent cage rings by means of connecting braces.
Figure 4C:
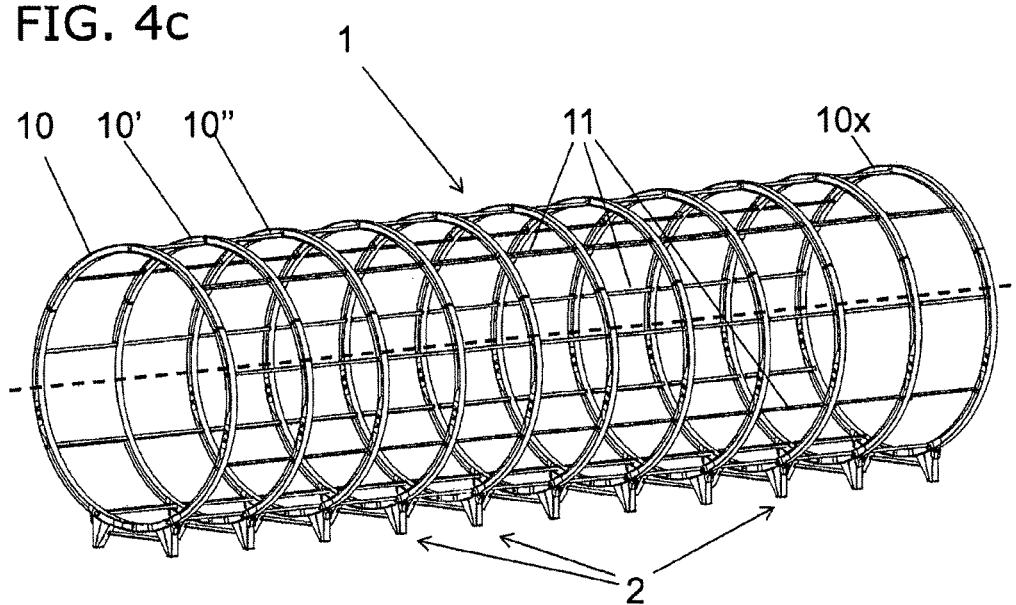
FIG. 4c shows a perspective view of a finished fermenter cage, comprising x cage rings.

FIGS. 4a to 4c now show the stepwise construction of the fermenter cage 1. The plurality of cage-retaining devices 2 is disposed horizontally on a plane with fixed distances. After being assembled from several ring segments 100, 100', 100", a first cage ring 10 is set up on a first cage-retaining device 2 vertically and thus perpendicularly to the subsequent longitudinal axis L. The outside surface of the cage ring 10 is in active connection with the rolling device 200, the guideway 201, and the support surface 203 of each holder 20. During the assembly process, the outside surface of the cage ring 10 rolls on the rolling device 200 such that the cage ring 10 is mounted rotatably about the subsequent longitudinal axis L of the fermenter 0. After the completed assembly, the finished fermenter cage 1 and the individual cage rings 10, respectively, are lowered onto the support surfaces 203 and thus held locally fixed and secured against rotation.

After setting up a first cage ring 10, a further cage ring 10' is set up vertically in active connection and rotatable on a further cage-retaining device 2, as shown in FIG. 4b. A plurality of connecting braces 11 is fixed to run between the directly adjoining cage rings 10, 10' so that the cage rings 10, 10' are prevented from falling over. As shown in FIG. 4c, the process of placing further cage rings 10" to 10x and connecting braces 11 is carried out until the fermenter cage 1 has the desired fermenter cage length. An arrangement of cage rings 10 to 10x in rows and connection to one another by means of connecting braces 11 is carried out. In total, the fermenter cage 1 shown here is formed by $x = 11$ cage rings 10 to 10x. By way of example, nine connecting braces 11 are arranged along the periphery of the fermenter cage 1 between two adjacent cage rings 10 to 10x. The connecting braces 11 are for this purpose fastened detachably, but more particularly permanently by welding to each adjoining cage ring 10 to 10x. The connecting braces 11 serve as a backup welding bar retainer for the subsequent blunt seam welding of adjacent shell plates.

Figure 5:
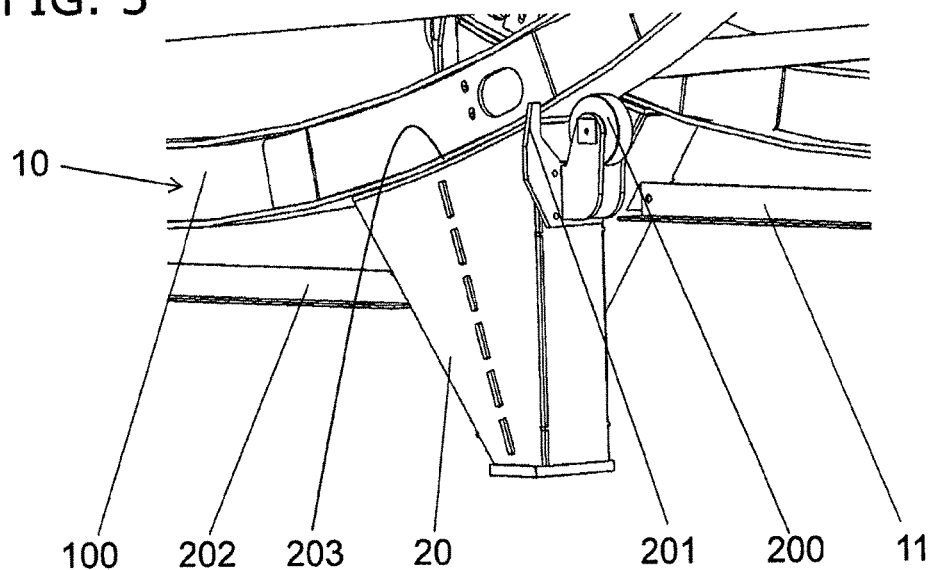
FIG. 5 shows a perspective detailed view of a holder, on which a cage ring is rotatably mounted by means of a rolling device.

FIG. 5 shows the support of a cage ring 10 in detail. The outside surface of the cage ring 10 is mounted movably on the holder 20 spaced from the support surface 203. The cage ring 10 can be rotated through interaction with the rolling device 200, which is here designed as a roller. The rolling device 200 spaces the outside surface of the cage ring 10 slightly away from the support surface 203, such that a rotation of the cage ring 10 is possible. The guideway 201 prevents the outside of the cage ring 10 from slipping laterally away from the rolling device 200 and the support surface 203.

After finishing the fermenter cage 1, the fermenter shell 3 is produced, which is formed from a plurality of n rows of shell plates 30 to 30n. The fermenter shell 3 forms a cylindrical sleeve face, wherein the fermenter shell 3 here lies inside the fermenter cage 1. In a first rotational position of the fermenter cage 1, shell plates 30 are introduced into the interior of the fermenter cage 1 in a first row in the longitudinal direction, thus parallel to the longitudinal axis L. The shell plates 30 are pre-curved through their inherent weight. However, an active bending of the first shell plates 30 corresponding to the path of the interior faces of the cage rings 10 must take place, for which an assembly aid is used. Good results could be achieved with shell plates 30, the thickness of which was smaller or equal to eight millimeters. Pre-curving can thereby be achieved, and the active bending on site can be carried out more easily. As soon as the desired curvature is reached the first shell plates 30 are fastened permanently, preferably by means of a welding process, to the interior faces of the cage rings 10 to 10x facing the interior of the fermenter cage.

The shell plates 30 can be connected to the interior face of the cage rings 10 to 10x by means of plug welding. The assembly aid can be released again after fastening the shell plates 30, while the shell plate 30 retains its curved form and a certain pretension results. The fermenter cage 1 is lined gas-tightly by the plurality of shell plates 30.

Figure 6A:
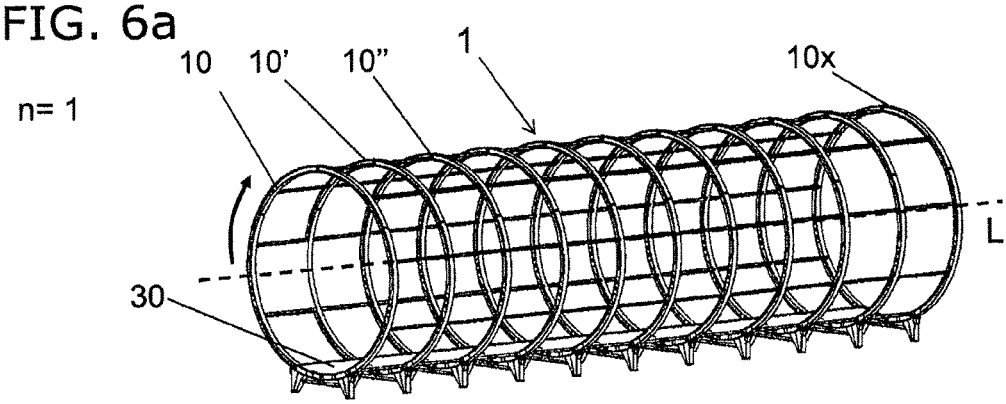
FIGS. 6 show the stepwise insertion and fastening of n rows of shell plates in perspective views, whereby after insertion and fastening of each row, the fermenter cage is rotated and a closed fermenter shell is created step by step.
Figure 6B:
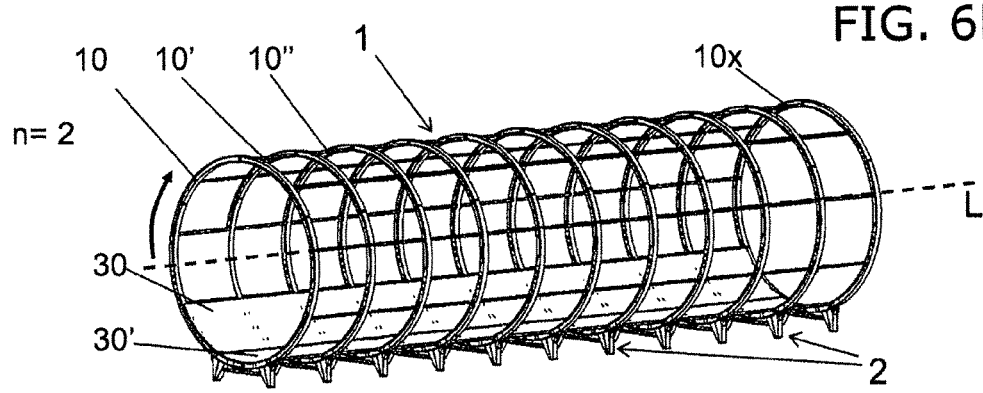

When the first row of shell plates 30 is fastened, the fermenter cage 1 is rotated, which is indicated by an arrow in FIG. 6a. Subsequently, the insertion, bending, and fastening of a further row of shell plates 30' can take place, as shown in FIG. 6b. The shell plates 30' are each welded to the cage rings 10 to 10x following transverse welding seams along the periphery of the cage rings 10 to 10x. Adjacent rows of shell plates 30, 30' are welded gas-tight to one another along a longitudinal welding seam S running in the direction of the longitudinal axis L. Since the fermenter cage 1 is rotatable, the longitudinal welding seam S can preferably be formed in the lower region of the cage rings 10 to 10x, facing the cage-retaining devices 2. It is thus possible to use a welding robot, which creates the longitudinal welding seams S.

As a result of the fermenter cage 1 being able to rotate, in order to simplify the welding processes the fermenter cage 1 can always be previously rotated into such a welding position that the longitudinal welding seam S between adjacent rows of shell plates 30 to 30n is welded in a position facing the cage-retaining devices 2 and thus in the region of each lowest point of the cylindrical fermenter cage 1. Overhead welding can thus be avoided.

In order to facilitate the fastening of the shell plates 30 to 30n of different rows to the cage rings 10 to 10x, a plurality of transverse slits Q can be provided in the shell plates 30 to 30n. These transverse slits Q are arranged in such a way that they come to rest on the internal faces of the cage rings 10 to 10x when the shell plates 30 to 30n are inserted in the fermenter cage 1. Fastening the shell plates 30 on the cage rings 10 to 10x can then take place by welding in the peripheral direction.

A further possibility for fastening the inserted shell plates 30 to 30n consists in a welding process, which takes place from outside of the fermenter cage 1. After bending the shell plates 30 to 30n, the shell plates are welded in the transverse direction from outside of the fermenter cage 1.

Figure 6C:
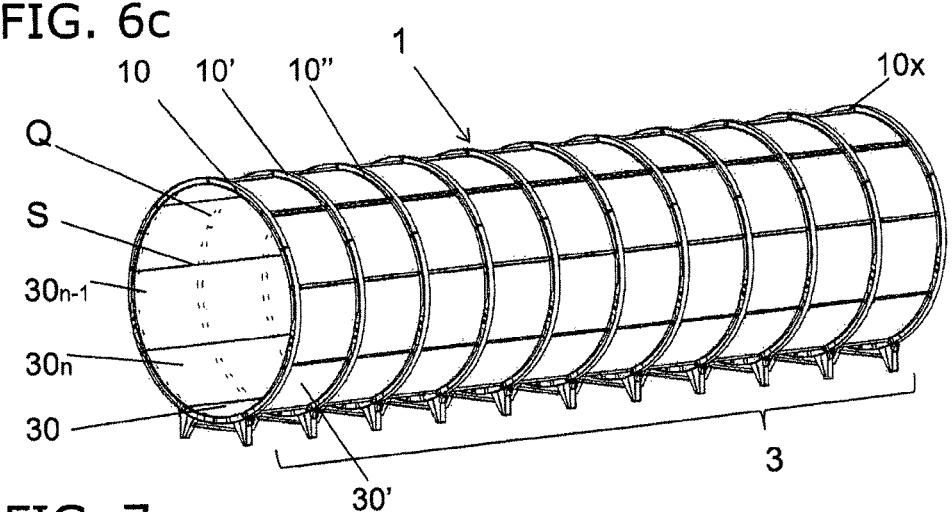

After welding on each row of shell plates 30, 30', the fermenter cage 1 will be rotated further, as shown in FIG. 6b. The rotation and the subsequent insertion, bending and fastening of further rows of shell plates to 30n is repeated until a fermenter shell 3 is reached that lines the entire cylindrical fermenter cage 1 completely gas-tight, as shown in FIG. 6c.

After finishing the fermenter cage 1 with the fermenter shell 3, the fermenter cage 1 can be closed off on the output side A with a wall structure 31 on the output side. This wall structure 31 on the output side is welded onto the last cage ring 10x or the shell plates 30n.

Figure 8:
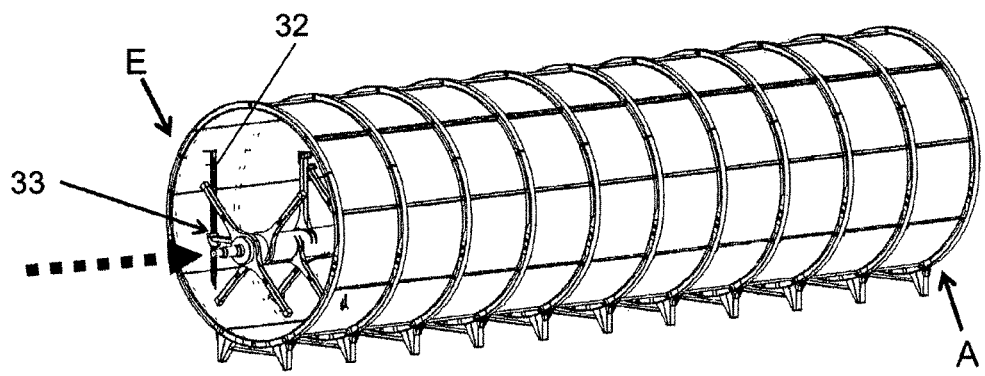
FIG. 8 shows a perspective view of the interior of the fermenter with the agitator unit fitted therein.
Figure 9:
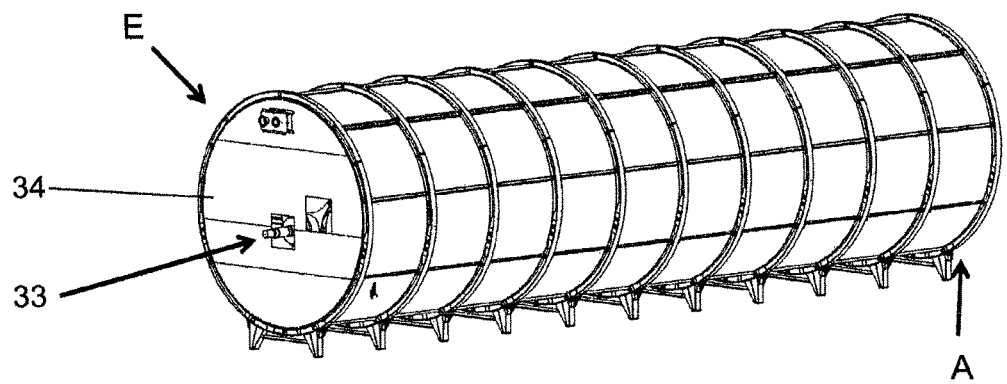
FIG. 9 shows the gas-tightly closed fermenter cage with fermenter shell, wall structure on the input side, agitator unit, and heating system.

By utilizing the ability of the fermenter cage 1 to rotate, a heating system 32 comprising several heating lances can also be inserted and fastened projecting into the interior of the fermenter cage. The path of the heating system 32 inside the fermenter cage can be seen in FIG. 8. The concentration of the heating lances is greater in the region of the input site E than in the region of the output side A. After suitable rotation of the fermenter cage 1 about the longitudinal axis L, the heating lances can be easily inserted.

Likewise after finishing the fermenter shell 3, an agitator unit 33 can be inserted into the interior of the fermenter cage and fastened there. The agitator unit 33 is here designed as a shaft, on which a plurality of agitator blades is arranged projecting radially outwards. The agitator unit 33 is inserted into the fermenter cage 1 from the input side E linearly in the direction of the longitudinal axis L, as indicated by the dotted arrow, and fastened. The input side E of the fermenter cage 1 is then closed in a gas-tight manner by a wall structure 34 on the input side, which is fastened to the first cage ring 10.

The fermenter cage 1, which is still rotatable and is lined with the fermenter shell 3 comprising n rows of shell plates 30 to 30n, is then rotated about the longitudinal axis L by means of a stepwise rotation of the fermenter cage 1 and is thereby provided with an insulation shell 4. This insulation shell 4 can be formed from several insulation elements 40, which are flexible or rigid and pre-formed. The use of prefabricated insulation elements 40 of foam or polystyrene is possible. Alternatively, the insulation shell 4 can be formed by directly spraying on a foam during rotation of the lined fermenter cage 1.

Figure 10A:
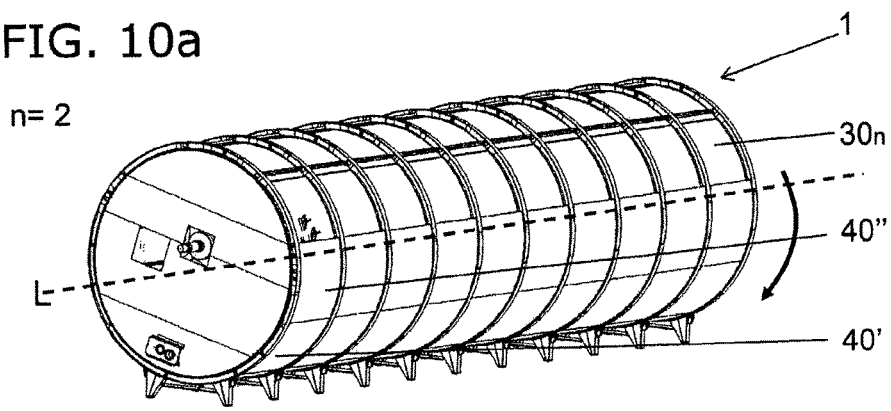
FIGS. 10 schemtically show illustrations of the fermenter cage during the assembly of an insulation shell with several rows of insulation elements, wherein the fermenter cage is rotated step by step after assembly of each row.
Figure 10B:
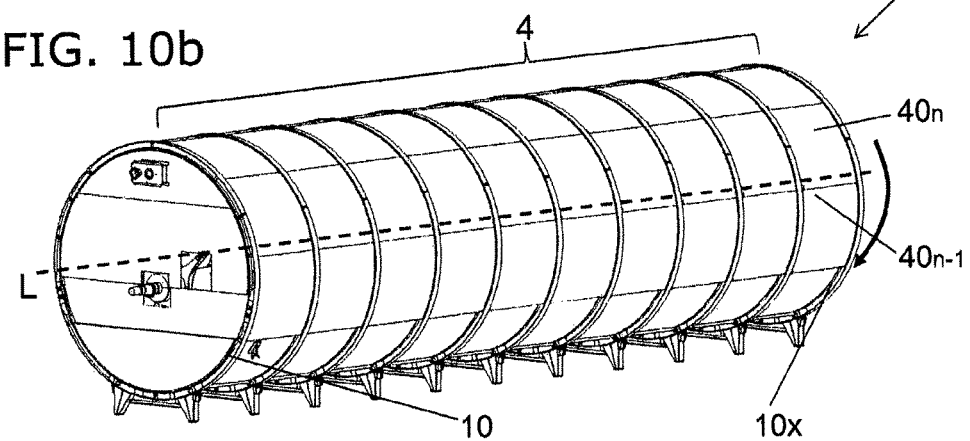

Rows of insulation elements 40 to 40n are attached to the fermenter shell 3 in a similar manner to when lining the fermenter cage 1 with shell plates 30 to 30n. After fastening a row of insulation elements 40' to the outside surface of the fermenter shell 3, the fermenter cage 1 undergoes a stepwise rotation about the longitudinal axis L, as shown by means of the arrow in FIG. 10a. A further row of insulation elements 40" can then be attached. The insulation elements 40 to 40n adapt to the outside surface of the fermenter shell 3. Attaching the insulation elements 40 to 40n and subsequently rotating the fermenter cage 1 is repeated until all the insulation elements 40 to 40n are arranged and fastened on the cylindrical sleeve face of the fermenter shell 3.

Individual insulation elements 40 to 40n could optionally also already be attached during finishing of the fermenter shell 3 after fastening the shell plates 30 to 30n. Preferably, however, the insulation shell 4 is only produced after completing the fermenter shell 3 and closing with the wall structure 31 on the output side and the wall structure 34 on the input side, by attaching individual rows of the insulation elements 40 and intermediate rotation of the fermenter about the longitudinal axis L.

After finishing the insulation shell 4, the fermenter 0 can be fastened in its operating position, as shown in FIG. 1. For this purpose, the rolling devices 200 of the cage-retaining devices 2 are removed and the outside faces of the cage rings 10 are lowered onto the support faces 203 and welded there. The fermenter cage 1 is then resting firmly on the cage-retaining devices 2. For further stabilization, the stabilizing supports 5 are fastened to the cage rings 10. Since the rolling devices 200 are no longer required once the fermenter shell 3 and the finished fermenter 0 have been fully constructed, they can be fastened detachably to the cage-retaining devices 2 and then removed again once the fermenter 0 is completely finished.

LIST OF REFERENCE NUMERALS

0 Fermenter
1 Fermenter cage
  10 cage rings (x pieces, 10 to 10x)
    100, 100',100" ring segment
      1000 connecting spot 11 connecting braces
2 Cage-retaining device (x pieces)
  20 holders each with a rolling device
    200 rolling device
      2000 wheel
    201 guideway
    202 retaining brace
    203 support surface
3 Fermenter shell
  30 to 30$n$ shell plate (n shell plate rows)
    300 transverse slits (recessed for welding)
    301 longitudinal seams (between directly adjacent shell plates)
  31 wall structure on output side
  32 heating system (heating lances in the edge region of the fermenter cage)
  33 agitator unit
  34 wall structure on input side
4 Insulation shell
  40 to 40$n$ insulation elements (n rows of insulation elements)
5 Stabilizing supports
L Longitudinal axis
E Input side
A Output side
Q Transverse slit
S Longitudinal welding seam

The invention claimed is:

1. A construction method of a fermenter with a fermenter cage and a fermenter shell of metal, for use in a biogas plant, wherein the fermenter cage is formed by a plurality of cage rings wherein each one cage ring is supported on at least one cage-retaining device, comprising at least one rolling device, so that the entire fermenter cage is mounted rotatably about a longitudinal axis, wherein the fermenter cage is rotated about the longitudinal axis while being lined with a plurality of rows of shell plates by means of rotation about the longitudinal axis, and the shell plates are permanently fastened to the plurality of cage rings and thus the gas-tight closed fermenter shell is formed step by step.

2. The construction method of a fermenter as claimed in claim 1, wherein the steps:
  I) introducing a first row of first shell plates into the fermenter cage parallel to the longitudinal axis,
  II) bending the first shell plates corresponding to a path of inner faces of the cage rings,
  III) permanently fastening the first shell plates to the inner faces of the cage rings facing an interior of the fermenter cage, and then
  IV) rotating the fermenter cage about the longitudinal axis so that an adjacent row of further shell plates can be placed in the fermenter cage next to the previously arranged shell plates and
  V) repeating steps I) to IV) until the nth row of shell plates is fastened and the fermenter cage is lined completely gas-tight by the fermenter shell, comprising n rows of shell plates.

3. The construction method of a fermenter as claimed in claim 2, wherein the manufacture of the fermenter cage is carried out by
  a) vertically placing several cage rings on cage-retaining devices with the rolling device such that the cage rings are arranged parallel to one another and are in active connection with the at least one rolling device so that a rotatable bearing of each cage ring is achieved and
  b) fastening several connecting braces between adjacent cage rings parallel to the longitudinal axis of a resulting fermenter cage and repeating the steps a) and b) until a desired fermenter cage length is reached.

4. The construction method of a fermenter as claimed in claim 1, wherein before or after finishing the fermenter shell a heating system projecting into an interior of the fermenter cage is arranged through rotation of the fermenter cage about the longitudinal axis.

5. The construction method of a fermenter as claimed in claim 1, wherein following the finishing of the fermenter shell an agitator unit is inserted into an interior of the fermenter cage and is fastened there through rotation of the fermenter cage about the longitudinal axis.

6. The construction method of a fermenter as claimed in claim 5, wherein the agitator unit is introduced into the fermenter cage from an input side linearly in the direction of the longitudinal axis.

7. The construction method of a fermenter as claimed in claim 1, wherein directly following the finishing of the fermenter shell a wall structure on an output side is permanently welded gas-tight onto the last cage ring and a wall structure on an input side is permanently welded gas-tight onto the first cage ring.

8. The construction method of a fermenter as claimed in claim 1, wherein prior to positioning, the cage rings are assembled together from a plurality of ring segments and connected to one another.

9. The construction method of a fermenter as claimed in claim 8, wherein the ring segments have flange plates at their ends, which are detachably connected to one another by means of bolts.

10. The construction method of a fermenter as claimed in claim 8, wherein the cage rings are assembled from three similar-sized ring segments.

11. The construction method of a fermenter as claimed in claim 1, wherein the cage rings are formed from double T-supports, which can be bent cold.

12. The construction method of a fermenter as claimed in claim 1, wherein prior to positioning the cage rings, the plurality of cage-retaining devices are arranged with rolling devices in one row.

13. The construction method of a fermenter as claimed in claim 1, wherein the shell plates do not exceed a thickness of eight millimeters.

14. The construction method of a fermenter as claimed in claim 1, wherein the fermenter cage is rotated into a welding position so that a longitudinal welding seam is welded between adjacent rows of shell plates in a position facing the cage-retaining devices.

15. The construction method of a fermenter as claimed in claim 14, wherein the welding of the rows of shell plates is carried out by a welding robot.

16. The construction method of a fermenter as claimed in claim 14, wherein transverse slits are arranged in the shell plates so that the transverse slits each come to lie on interior faces of the cage rings when the shell plates are inserted in the fermenter cage.

17. The construction method of a fermenter as claimed in claim 14, wherein after fixing the shell plates on the cage rings, the longitudinal welding seam between directly adjacent rows of shell plates is welded gas-tight.

18. The construction method of a fermenter as claimed in claim 1, wherein after closing the fermenter shell, an insulation shell is attached and fastened on the fermenter shell through rotation of the fermenter cage about the longitudinal axis.

19. The construction method of a fermenter as claimed in claim 18, wherein the insulation shell is formed by a plurality of rigid or flexible insulation elements or by a foam.

\* \* \* \* \*